United States Patent [19]

Iwamatsu et al.

[11] 4,160,026
[45] Jul. 3, 1979

[54] ANTIBIOTICS SF-1130-$X_1$ AND -$X_2$ SUBSTANCES AND PRODUCTION AND USE THEREOF

[75] Inventors: Katsuyoshi Iwamatsu, Kanagawa; Shoji Omoto, Tokyo; Takashi Shomura; Hiroshi Watanabe, both of Yokohama; Michio Kojima, Tokyo; Shigeharu Inoue, Yokohama; Taro Niida, Yokohama; Takashi Hisamatsu, Yokohama; Shingo Uchida, Yokohama, all of Japan

[73] Assignee: Meiji Seika Kaisha, Ltd., Tokyo, Japan

[21] Appl. No.: 826,766

[22] Filed: Aug. 22, 1977

[30] Foreign Application Priority Data

Aug. 23, 1976 [JP] Japan .................................. 51/99757

[51] Int. Cl.$^2$ .......................... C12D 9/14; A61K 35/74
[52] U.S. Cl. ........................................ 424/116; 435/84; 435/886

[58] Field of Search .................... 195/80 R; 424/116

[56] References Cited

U.S. PATENT DOCUMENTS 3,564,090  2/1971  Umezawa et al. .................... 195/80

Primary Examiner—Alvin E. Tanenholtz
Attorney, Agent, or Firm—Haight & Huard

[57] ABSTRACT

New antibiotics SF-1130-$x_1$ substance and SF-1130-$x_2$ substance are produced by cultivating a microorganism *Streptomyces myxogenes* SF-1130 now deposited under FERM-P. 676 and ATCC. 31305 in a liquid culture medium under aerobic conditions, and these antibiotics may be isolated from the fermentation broth and are useful as an activator for enhancing the host defense system in living animals. The activity of these antibiotics may be improved when used in combination with one or more of maltose, maltotriose, maltotetraose, maltopentaose, maltohexaose and maltoheptaose.

11 Claims, 4 Drawing Figures

ANTIBIOTICS SF-1130-$X_1$ AND -$X_2$ SUBSTANCES AND PRODUCTION AND USE THEREOF

SUMMARY OF THE INVENTION

This invention relates to a process for the production of new antibiotics designated as SF-1130-$x_1$ substance and SF-1130-$x_2$ substance by incubating a strain of the genus Streptomyces. This invention also relates to these antibiotics as the new and useful compounds and to the use of them as a stimulator for enchancing the host defense, in particular, immunological response in living animals and men.

BACKGROUND OF THE INVENTION

A number of useful substances are produced in and isolated from the culture broth of various strains of the genus Streptomyces. It is known that *Streptomyces myxogenes* SF-1130 (identified as FERM-P. 676) produces an antibiotic called SF-1130 substance (see Japanese Patent Publication No. 30393/73). We have made further research on the fermentation broth of the microorganism *Streptomyces myxogenes*, SF-1130, and we have now found that new antibiotic substances active against gram-negative bacteria are produced in the fermentation broth of said microorganism. We have succeeded in isolating these active substances from the broth and have designated them as SF-1130-$x_1$ substance and SF-1130-$x_2$ substance, respectively.

We have further found that these two active substances exhibit an activity by which the immunity inherently involved in living animals and man is prevented from being reduced more or less due to the formation of a tumor and/or due to the administration of an immunosuppressive anti-tumor agent, and that these active substances are hence useful as an immunopotentiator for enhancing the immune response in living animals and men.

An object of this invention is to provide new antibiotics which are useful as an antibacterial agents and as an activator for enhancing the immunity in living animals and men. A further object of this invention is to porvide a process of producing these useful substances. Other objects will be clear from the following descriptions.

DETAILED DESCRIPTION OF THE INVENTION

According to a first aspect of this invention, therefore, there is provided a process for the production of new antibiotics, SF-1130-$x_1$ substance and SF-1130-$x_2$ substance, which comprises cultivating a strain of the genus Streptomyces capable of producing SF-1130-$x_1$ substance and/or SF-1130-$x_2$ substance in an aqueous liquid culture medium containing assimilable carbon and nitrogen sources under aerobic conditions for a period of time sufficient to produce and accumulate the SF-1130-$x_1$ substance or SF-1130-$x_2$ substance or both of them in the culture, and then recovering at least one of the SF-1130-$x_1$ and SF-1130-$x_2$ subtances from the culture.

In carrying out the process of this invention, any strain of the genus Streptomyces may be used so long as it substantially produces the SF-1130-$x_1$ substance and/or SF-1130-$x_2$ substance. A specific example of the strain which may be suitably used in the present process is the SF-1130 strain which was isolated from a soil sample and which has been designated as *Streptomyces myxogenes* SF-1130. This SF-1130 strain has been deposited in a Japanese public depository "Fermentation Research Institute", Chiba-city, Japan under deposit number FERM-P. 676 and also in the American Type Culture Collection, Washington D.C., U.S.A., under deposit number ATCC. 31305.

The SF-1130 Strain has the following microbiological characteristics:

1. Morphological observation

Substrate mycelia are well grown on various culture media, while the formation of aerial mycelia is generally poor. On starch-agar, starch-yeast extract or starch-yeast extract-agar media where aerial mycelia develop, short and dense aerial mycelia are formed from the substrate mycelia which have well grown to long lengths. The substrate mycelia produce monopodially branches, no whorl-branching being observed.

The aerial mycelia bear at their tips spirals, most of which are of the compact closed type and some of which are of the incomplete or open type. No formation of sclerotium is observed. Electron-microscopic observation shows that the surface structure of the spores is smooth. The spores are of elliptical or cylindrical shape and have a size of 0.6–0.7 microns by 0.9–1.0 microns.

2. Cultural characteristics on various culture media are set out in Table 1 below:

Table 1

| Culture medium | Growth | Aerial mycelium | Soluble pigment |
| --- | --- | --- | --- |
| Sucrose-nitrate agar | Poor growth, colorless | Poor, white | None |
| Glucose-asparagine agar | Brown to greyish brown, reverse side faintly tinged with red color | None | None |
| Glycerol-asparagine agar | Brown | None | None |
| Calcium malate agar | Thin growth, pale brown | None | None |
| Glycerol-calcium malate agar | Brown | None | None |
| Starch agar | Pale brown to brown | Powdery, greyish brown, development mainly at periphery of colony | None |
| Oatmeal agar | Good, pale brown | Grey | None |
| Nutrient agar | Good growth with wrinkles, brown reverse side | None | Brown |
| Starch-yeast extract-agar | Pale brown to brown | Greyish brown to grey | Pale brown |
| Yeast-malt-agar | Good, reddish brown | None | Brown Blackish |
| Tyrosine agar | Dark brown | None | brown |
| Potato plug | Raised growth with wrinkles, brown | None | Brown |
| Carrot plug | Greyish brown growth with wrinkles | None | Pale brown |
| Gelatine (20° C.) | Cream color | None | Dark brown to black |
| Skimmed milk (37° C.) | Bottom growth, pale brown | None | None |

Table 1-continued

| Culture medium | Growth | Aerial mycelium | Soluble pigment |
| --- | --- | --- | --- |
| Loeffler's coagulated serum (37° C.) | Dark grey | None | None Grey pigment at periphery of the growth |
| Egg (37° C.) | Dark grey to dark brown | None | |
| Glucose-Czapek's solution | Bottom growth, cream | None | None |
| Cellulose | No growth | — | — |

Note: The incubation temperature was 28° C. unless otherwise indicated.

3. Physiological properties

| | |
| --- | --- |
| Liquefaction of gelatine | = Positive |
| Hydrolysis of starch | = Positive |
| Production of tyrosinase | = Positive |
| Production of hydrogen sulfide | = Positive |
| Chromogenicity | = Positive |
| Degradation of cellulose | = Negative |
| Reduction of nitrate | = Negative |
| Peptonization of skimmed milk | = Negative |
| Cogulation of skimmed milk | = Negative |
| Dissolution of Loeffler's coagulated serum | = Negative |

In addition to the above-mentioned physiological properties, the SF-1130 strain produces mucilage on agar medium and in a liquid medium, which is an important feature of the subject strain.

On an agar medium such as starch-yeast extract-agar, starch-agar or glucose-asparagine-agar medium, it is observed that the mucilage is produced massively on the colony at nearly 10 days of incubation. It is also observed that when the SF-1130 strain is shake-cultivated in a liquid medium containing suitable carbon sources (glucose, starch etc.) and nitrogen sources (yeast extract, soybean meal, wheat embryo etc.), then the culture broth gradually becomes viscous with formation of a mucilage.

4. Utilization of carbon sources (1) Utilized: xylose, glucose, galactose, maltose, sucrose, lactose, raffinose, dextrin, starch, glycerol, inositol, sodium acetate, sodium citrate and mannose.

(2) Doubtful: arabinose, fructose and salicin.

(3) Not utilized: rhamnose, inulin, dulcitol mannitol, sorbitol, sodium succinate and cellulose.

The aforesaid microbiological characteristics of the SF-1130 strain may be summarized as follows:

(1) The aerial mycelium forms closed spirals at its tip and the surface structure of the spore is smooth.

(2) The aerial mycelium, which is greyish brown to grey in color, is produced very poorly.

(3) The growth on synthetic culture media is brown to greyish brown in color.

(4) On organic culture media, chromogenicity is observed.

(5) Mucilage is produced on agar medium and liquid media.

In view of the microbiological characteristics described above, there may be mentioned *Streptomyces pheochromogenes*, *Streptomyces pulpreochromogenes* and *Streptomyces noborytoensis* as known strains analogous to the SF-1130 strain. However, the SF-1130 strain is not coincident with any of these known strains as illustrated below:

*Streptomyces phoechromogenes* produces abundant aerial mycelia and forms brown soluble pigment on sucrose-Czapek's agar and calcium malate-agar media, while the SF-1130 strain shows poor production of aerial mycelis and no formation of soluble pigment on the aforesaid agar media.

*Streptomyces pulpreochtomogenes* produces orange to reddish orange colored growth on potato plug medium, forms no hydrogen sufide and causes coagulation of skimmed milk. In contrast, the SF-1130 strain produces brown gowth on the same medium and causes formation of hydrogen sulfide but no coagulation of skimmed milk.

*Streptomyces noborytoensis* forms no spiral and produces green soluble pigment on starch-agar medium (the production of green soluble pigment is not mentioned in the prior documents, but, in fact, appreciably observed for the type-culture strain), whereas the SF-1130 strain forms spirals but produces no soluble pigment on starch-synthetic agar. Moreover, the SF-1130 strain is distinguishable from *Streptomyces noborytoensis* also in utilization of mannitol and sucrose.

Thus, the SF-1130 strain is clearly differentiated from any of the known related species of the genus Streptomyces. The SF-1130 strain is further distinctive from any known species of Streptomyces in that the former exhibits the peculiar properties of producing mucilage as already stated, while the latter produces no mucilage according to prior reports.

In consequence, the SF-1130 strain was identified as a new species of the genus Streptomyces and designated as "*Streptomyces myxogenes* nov. sp.".

The SF-1130 strain has properties which are liable to vary as may be usually observed with other species of Streptomyces. Thus, for example, the SF-1130 strain may produce variants or mutants when treated with various mutagens such as ultraviolet rays, X-rays, high-frequency electromagnetic waves, radioactive rays and chemicals. Therefore, any strain of the genus Streptomyces, including any natural or artificial variant and mutant of the aforesaid SF-1130 strain, may be used in the process of this invention, so long as it has the ability to produce the SF-1130-$x_1$ substance or the SF-1130-$x_2$ substance or both of them (hereinafter, either one or both of these two substances is or are sometime called merely as the SF-1130-x substance).

In carrying out the process of this invention, the strain for present use may be cultivated in a manner known per se in a culture medium containing nutrient sources which are assimilable by ordinary microorganisms. For this purpose, use may be made of any known nutrients which have been generally employed for the cultivation of known strains of the genus Streptomyces. Examples of the nutrient sources include glucose, starch, starch syrup and molasses as the carbon sources; and soybean meal, wheat embryo, dried yeast, peptone, meat extract, corn steep liquor, ammonium sulfate and sodium nitrate as the carbon sources. If required, inorganic salts such as calcium carbonate, sodium chloride, potassium chloride, phosphates and the like may be added. In addition such organic and inorganic materials as aid the growth of the strain used and promote the production of the SF-1130-x substance may be incorporated in the culture medium.

As the cultivation methods which can be employed in this invention, liquid cultivation, particularly under submerged aerobic conditions, is most preferred as is generally used in the production of known antibiotics. In the present process, the cultivation is conducted under aerobic conditions, suitably at a temperature of 25° to 38° C. and most frequently at a temperature in the vicinity of 28° C. In this situation, the production of the SF-1130-x substance in the culture broth reaches a maximum at the end of 2 to 5 days of fermentation, either in shake-cultivation methods or in tank-cultivation methods.

For assay of the SF-1130-x substance of this invention, the following procedure may be used: the assaying culture medium comprising 0.5% peptone, 0.3% meat extract and 1.5% agar, (pH 6) (known as the mycin-assaying agar medium) together with 0.125% maltotriose is used. As the assaying microorganism is used *Escherichia coli* K-12R. The assay may usually be conducted according to the conventional paper-disc method.

The SF-1130-x substance of this invention is an oligosaccharide of weakly basic nature which has physio-chemical properties as stated hereinafter, and hence by taking advantage of the physio-chemical characteristics of the SF-1130-x substance, it can be recovered from the culture broth and then purified. For instance, the purification may be achieved according to adsorption on carbon, chromatography using aqueous alcohol as the eluent or re-precipitation from mixed solvent of water-ethanol.

For instance, the SF-1130-x substance can be recovered from the fermentation broth and isolated by the following procedure: The fermentation broth containing the SF-1130-x substance is acidified to pH 3 by addition of e.g sulfuric acid or hydrochloric acid and then filtered under acidic conditions to remove the mycelia and insoluble matter, and the broth filtrate is passed through a column of active carbon for adsorption of the active substances. The carbon column is then eluted with 50% acetone-water (i.e., a mixture of acetone and water at ratio of 1:1 by volume) to desorb the SF-1130-x substance from the active carbon. The eluate is concentrated to dryness and the residue is dissolved in water. The resulting aqueous solution is again passed through a column of active carbon for adsorption, and the carbon column is then eluted successively with aqueous solutions containing ethanol at different concentrations in the range of 5 to 25% by volume. The eluate is collected in fractions, and those antibacterially active fractions containing the SF-1130-x substance are combined together and concentrated. To the concentrated solution is added a volume of ethanol to precipitate the SF-1130-x substance which is easily recovered as a crude powder. The curde powder obtained in the above way normally contains a substantial proportion of neutral oligo-saccharides and particularly maltodextrin which are co-produced in the fermentation broth. In order to obtain a high-purity product of the SF-1130-x substance, therefore, it is rather preferred to employ the following procedure of recovery: Thus, the fermentation broth of the SF-1130 strain containing the SF-1130-x substance or the broth filtrate obtained therefrom is passed through a column of a strongly acidic cation-exchange resin such as Dowex 50W×2 (H+ form) (a produce made by Dow Chemical Co., U.S.A.) for adsorption of the SF-1130-x substance. The resin column is well washed with water to remove therefrom traces of the neutral oligo-saccharides such as maltodextrin, maltopentaose and maltohexaose which have been occasionally attached to the resin from the fermentation broth. After the washing, the resin column is eluted with 0.1 N aqueous ammonia for desorption of the SF-1130-x substance. The eluate is concentrated to dryness and the residue is dissolved in water. The resulting aqueous solution is adjusted to pH 3.5 by addition of sulfuric or hydrochloric acid and then passed through a column of active carbon for adsorption of the SF-1130-x substance. The carbon column is washed with water and then eluted with an aqueous solution containing 30–35% ethanol. The eluate is concentrated to dryness, the residue is dissolved in water and the solution so obtained is again passed through a column of a cation-exchange resin such as Dowex 50W×2($NH_4^+$ form). The resin column is washed with water and eluted with 0.1 N aqueous ammonia. The eluate is concentrated to dryness, the residue is dissolved in water and the aqueous solution so obtained is subjected to a chromatography on a cation-exchange resin such as Dowex 50W×2 (pyridinum salt form) using 0.1 M pyridine-formic acid buffer (pH 3.1) as the development solvent. The eluate is collected in fractions, and the antibacterially active fractions are combined together and concentrated to dryness to give a colorless powder comprising the SF-1130-x substance in the form of a mixture of the SF-1130-$x_1$ and SF-1130-$x_2$-substances. This crude powder may be provided as such for conducting the test of estimating the physiological properties of the SF-1130-x substance. For the isolation of the SF-1130-$x_1$ and -$x_2$ substances, if necessary, the aforesaid colorless powder comprising the mixture of these substances is taken up into water and the resulting aqueous solution is sujected to a chromatography in a column of cellulose using mixed solvent of n-propanol-ethyl acetate-water (6:1:3 by volume) as the development solvent. The eluate is collected in fractions, and those fractions which give a single spot at an $R_{raffinose}$ value of 0.39 (calculated as assumed that the $R_f$ value of raffinose is 1.00) in paper-chromatography developed with ethyl acetate-pyridine-water (10:4:3 by volume) are combined together and concentrated to dryness to afford the SF-1130-$x_1$ substance as colorless powder. The SF-1130-$x_2$ substance is isolated as colorless powder when those fractions which give a single spot at an $R_{raffinose}$ value of 0.57 in the same paper chromatography are combined together and concentrated to dryness.

In case the process of this invention is conducted using the SF-1130 strain as mentioned above, the resulting culture broth contains, in addition to the SF-1130-$x_1$ and -$x_2$ substances, the known antibiotic SF-1130 substance (see Japanese Patent Publication No. 30393/73) as well as maltopentaose and maltohexaose which are produced by the SF-1130 strain (see pending Japanese patent application No. 99756/76). The SF-1130 substance is a neutral oligo-saccharide which is readily soluble in water, sparingly soluble in methanol and ethanol but not soluble in acetone, while maltopentaose and maltohexaose are neutral oligo-saccharides which are readily soluble in water, sparingly soluble in methanol but not soluble in ethanol and acetone. In contrast, The SF-1130-$x_1$ and -$x_2$ substances of this invention are oligo-saccharides of basic nature which are readily soluble in water, less soluble in methanol and ethanol but not soluble in acetone. By taking advantage of these differences in the properties of the above-mentioned new and known substances, the SF-1130-$x_1$ and -$x_2$ substances can be separated from the SF-1130 substance as well as from maltopentaose and maltohexaose. For instance, the fermentation broth of the SF-1130 strain is acidified by addition of a suitable inorganic acid such as hydrochloric or sulfuric acid and filtered. When the acidified broth filtrate so obtained is passed through a column of a strongly acidic cation-exchange resin such as Dowex 50W×2 (H+ form), the SF-1130-$x_1$ and -$x_2$ substances are adsorbed by said resin, whereas the neutral oligo-saccharides such as maltopentaose and maltohexaose are passed through the resin column without being adsorbed by the resin. When the resin containing the SF-1130-x substance adsorbed therein is treated with 0.1 N aqueous ammonia as eluent, the SF-1130-x substance is eluted out of the resin.

The SF-1130-$x_1$ and -$x_2$ substances obtained by the process of this invention are the new and useful substances as stated hereinbefore and illustrated hereinafter.

According to a second aspect of this invention, therefore, there is provided a substance selected from the group consisting of SF-1130-$x_1$ substance and SF-1130-$x_2$ substance which are each an oligo-saccharide of weakly basic nature in the form of colorless powder, which are each soluble in water and dimethylsulfoxide, less soluble in methanol and ethanol but insoluble in acetone, ethyl acetate, chloroform and benzene, which each show positive reaction with silver nitrate, red tetrazolium, anthrone, ninhydrin and Greig-Leaback reagents and which are each hydrolyzable with acid to give glucose; the SF-1130-$x_1$ substance being further characterized by:

(a) exhibiting an elemental analysis: C 43.65%, H 6.55%, N 1.05% and O 49.75% (balance);

(b) having a specific optical rotation $[\alpha]_D^{23} + 166°$ (c 1 in water);

(c) having no characteristic adsorption peak in ultraviolet adsorption spectrum;

(d) having an infrared adsorption spectrum pelleted in potassium bromide corresponding to that shown in FIG. 1a of the attached drawings;

(e) having a hydrogen nuclear magnetic resonance absorption spectrum in deutero-water corresponding to that shown in FIG. 2a of the attached drawings; and (f) giving a single spot at $R_{raffinose}=0.39$ in paper-chromatography with ethyl acetate-pyridine-water (10:4:3) as the developing solvent and at $R_{raffinose}=0.19$ in paper-chromatography with n-butanol-pyridine-acetic acid-water (6:4:1:3) as the developing solvent when the $R_{raffinose}$ values are calculated as assumed that raffinose gives a single spot at Rf=1.00 in the same paper chromatography; and the SF-1130-$x_2$ substance being further characterized by:

(a) exhibiting an elemental analysis: C 43.84%, H 6.41%, N 1.08% and O 49.67% (balance);

(b) having a specific optical rotation $[\alpha]_D^{23} + 155°$ (c 1 in water);

(c) having no characteristic absorption peak in ultraviolet absorption spectrum;

(d) having an infrared absorption spectrum pelleted in potassium bromide corresponding to that shown in FIG. 1b of the attached drawings;

(e) having a hydrogen nuclear magnetic resonance spectrum in deutero-water corresponding to that shown in FIG. 2b of the attached drawings; and (f) giving a single spot at $R_{raffinose}=0.57$ in paper-chromatography with ethyl acetate-pyridine-water (10:4:3) as the developing solvent and at $R_{raffinose}=0.33$ in paper-chromatography with n-butanol-pyridine-acetic acid-water (6:4:1:3) as the developing solvent when the $R_{raffinose}$ (values are calculated as assumed that raffinose gives a single spot at $R_f = 1.00$ in the same paper chromatography.

The above-mentioned and further physico-chemical properties of the SF-1130-$x_1$ and SF-1130-$x_2$ substances of this invention are shown in Table 1 below.

In view of the facts that the SF-1130-$x_1$ and -$x_2$ substances are adsorbable by an acidic ion-exchange resin and movable toward the cathode at pH 1.9 in a filter paper electrophoresis and that these substances are hydrolyzable with acid to give a substantial amount of glucose, it is considered that they are oligo-saccharides of weakly basic nature.

Table 1

| Properties | SF-1130-$x_1$ | SF-1130-$x_2$ |
| --- | --- | --- |
| Appearance | Colorles, odorless amorphous powder | Colorless, odorless amorphous powder |
| Melting point | 203° C. (with decomposition) | 195° C. (with decomposition) |
| Elemental analysis (%) | C: 43.65<br>H: 6.55<br>N: 1.05 | C: 43.84<br>H: 6.41<br>N: 1.08 |
| Molecular weight (as determined by vapor pressure method) | 1100 | 900 |
| Specific optical rotation | $[\alpha]_D^{23} + 166°$ (c 1, water) | $[\alpha]_D^{23} + 155°$ (c 1, water) |
| Ultraviolet absorption spectrum | No characteristic absorption peak | No characteristic absorption peak |
| Infrared absorption spectrum | Shown in Figure 1a | Shown in Figure 1b |
| Hydrogen nuclear absorption spectrum | Shown in Figure 2a | Shown in Figure 2b |
| Solubility Soluble in: | water, dimethylsulfoxide | water, dimethylsulfoxide |
| Less soluble in: | methanol, ethanol, | methanol, ethanol |
| Insoluble in: | acetone, ethyl acetate, chloroform, benzene | acetone, ethyl acetate, chloroform, benzene |
| Stability | Stable under neutral conditions but somewhat instable under acidic and alkaline conditions | Stable under neutral conditions but somewhat instable under acid and alkaline conditions |
| Color Reaction Positive to: | Silver nitrate, red tetrazolium, anthrone, ninhydrin and Greig-Leaback reagents | Silver nitrate, red tetrazolium, anthrone, ninhydrin and Greig-Leaback reagents |
| $R_{rafinose}$ values in paper chromatograph (as assumed that $R_f$ of raffinose is 1.00) | | |
| i) Developed with ethyl acetate-pyridine-water (10:4:3) | 0.39 | 0.57 |
| ii) Developed with n-butanol-pyridine-acetic acid-water (6:4:1:3) | 0.19 | 0.33 |

Referring to the attached drawings.

shown in Table 2. It is to be noted that maltotriose and other maltodextrins do not exhibit any antibacterial activity under the above-mentioned testing conditions.

Table 2

| | Diameter of Inhibition zone (mm) with SF-1130-$x_1$ substance | | | | Diameter of Inhibition zone (mm) with SF-1130-$x_2$ substance | | | |
|---|---|---|---|---|---|---|---|---|
| | No additional use of maltotriose | | Additional use of maltotriose | | No additional use of maltotriose | | Additional use of maltotriose | |
| | Level of SF-1130-$x_1$ | | | | Level of SF-1130-$x_2$ | | | |
| Test microorganism | 2mg/cc | 1mg/cc | 2mg/cc | 1mg/cc | 2mg/cc | 1mg/cc | 2mg/cc | 1mg/cc |
| Escherichia coli IAM 1239 | 0 | 0 | 15.9 | 15.0 | 0 | 0 | 14.8 | 14.2 |
| Escherichia coli K-12 | 11.4 | 0 | 19.5 | 16.0 | 13.0 | Minor | 18.8 | 15.3 |
| Escherichia coli (resistant to chloramphenicol) | 14.2 | 13.6 | 23.2 | 19.8 | 14.5 | 13.4 | 23.6 | 20.9 |
| Escherichia coli IAM 1264 | 15.9 | 12.1 | 26.1 | 24.0 | 15.2 | 12.8 | 25.4 | 23.6 |
| Shigella sonnei | 13.5 | Minor | 20.0 | 18.0 | 13.0 | 0 | 19.3 | 17.8 |
| Proteus vulgaris | Minor | 0 | 15.9 | 12.8 | Minor | 0 | 15.4 | 12.8 |
| Salmonella typhi | 13.7 | 12.0 | 20.1 | 18.3 | 13.4 | 11.4 | 19.0 | 17.6 |
| Klebsiella pneumoniae | 15.0 | 12.3 | 15.1 | 12.0 | 13.2 | 11.5 | 13.2 | 11.0 |
| Bacillus subtilis | 0 | 0 | 0 | 0 | 0 | 0 | 0 | 0 |
| Staphylococcus aureus | 0 | 0 | 0 | 0 | 0 | 0 | 0 | 0 |
| Sarcina lutea | 0 | 0 | 0 | 0 | 0 | 0 | 0 | 0 |
| Mycobacterium smegmatis 607 | 0 | 0 | 0 | 0 | 0 | 0 | 0 | 0 |

Figure 2A:
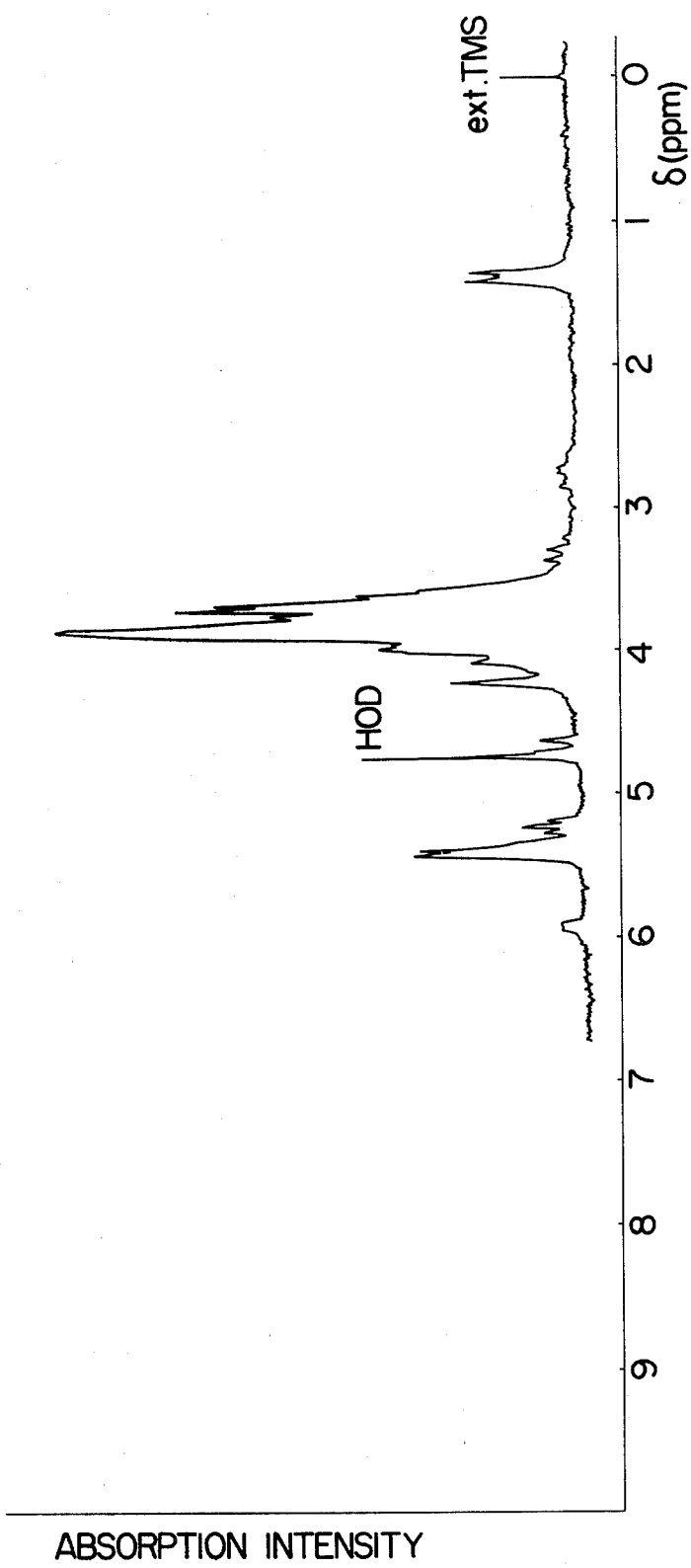

FIG. 2a shows a curve of the hydrogen nuclear magnetic resonance absorption spectrum of sample of the SF-1130-$x_1$ substance determined in deutero-water at 100 MHz.

Figure 2B:
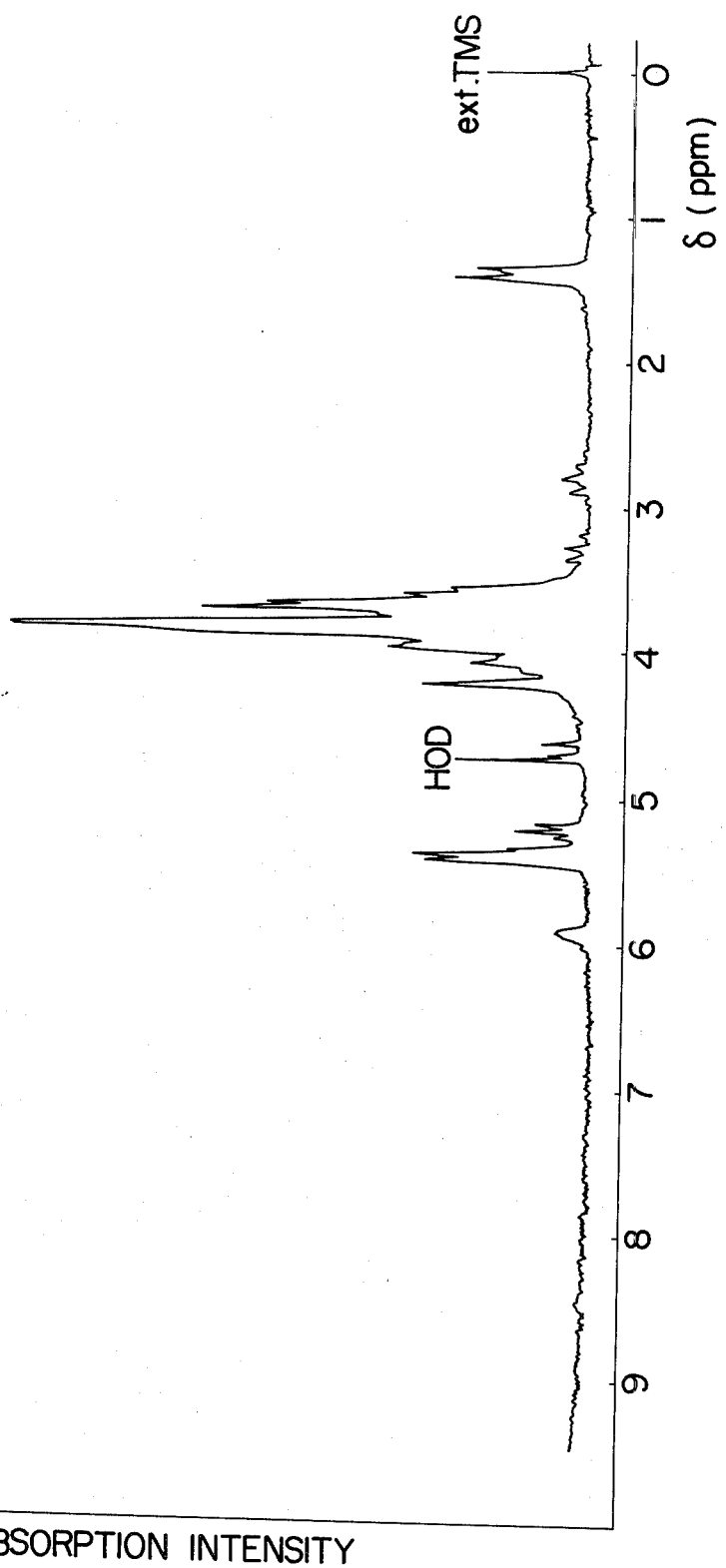

FIG. 2b shows a curve of the hydrogen nuclear magnetic resonance absorption spectrum of sample of the SF-1130-$x_2$ substance determined in deutero-water at 100 MHz.

The antibacterial activity of the SF-1130-$x_1$ and SF-1130-$x_2$ substances to inhibit the growth of various bacteria was estimated according to a conventional paper disc plate method. Thus, the SF-1130-$x_1$ substance or SF-1130-$x_2$ substance was dissolved in distilled water at a concentration of 1 mg/cc or 2 mg/cc, and with the test solutions so prepared were impregnated paper discs made of filter paper of 8 mm in diameter which were subsequently air-dried. These paper discs were placed on an upper plate layers of the known mycin-assay incubation medium comprising 0.5% peptone, 0.3% meat extract and 1.5% agar (pH 6) which contained the test microorganism to be incubated therein and which was laid over the lower layer of agar medium in the assaying dish. The incubation was made at a temperature of 37° C. overnight, and subsequently the diameter of the inhibition zones formed around the paper discs was measured. The test results so obtained are shown in Table 2 below, from which it is found that the SF-1130-$x_1$ and SF-1130-$x_2$ substances have no antibacterial activity against the gram-positive bacteria and acid-fast bacteria. These tests were repeated in the same manner as above but with additional incorporation of 1.25 mg/cc of maltotriose into the upper plate layer of the mycin-assay incubation medium. The test results so obtained are also shown in Table 2, from which we have discovered that the additional presence of maltotriose improves the antibacterial activity of the SF-1130-$x_1$ and -$x_2$ substances. In similar tests, we have further found that when maltose or a maltodextrin, including maltotriose, maltotetraose, maltopentaose and maltohexaose is used in combination with the SF-1130-$x_1$ or SF-1130-$x_2$ substance, the former generally improves the anti-bacterial activity of the latter, too, with an exception that the improvement in the antibacterial activity is not observed against Klebsiella pneumoniae. All the results of the tests conducted in this respect are From the results of further tests, we have now found that the improvement in the antibacterial activity of the SF-1130-$x_1$ substance or the SF-1130-$x_2$ substance owing to the additional or combined use of maltose, maltotriose, maltotetraose, maltopentaose or maltohexaose is significant when maltose or the maltodextrin as mentioned above is additionally used in a proportion ranging from 0.1 to 20 parts by weight per one part by weight of the SF-1130-$x_1$ or -$x_2$ substance.

To estimate acute toxicity of the SF-1130-$x_1$ and -$x_2$ substances, aqueous solutions of the SF-1130-$x_1$ or -$x_2$ substance were injected subcutaneously to mice; all mice tested survived at the doses of up to 400 mg/kg. From the results of further tests for acute toxicity, it has been found that the SF-1130-$x_1$ and -$x_2$ substances have and $LD_{50}$ value of not more than 500 mg/kg upon intravenous injection in mice. Accordingly, it is clear that the SF-1130-$x_1$ and -$x_2$ substances are each of very low toxicity.

Cell-mediated immunity tests were carried out according to a known delayed hypersensitivity technique using mice inoculated with an ascites tumor "Sarcoma 180", and from the results of tests obtained it has been found that the SF-1130-$x_1$ and -$x_2$ substances have the immuno-potentiating effect in tumor-bearing animals whose immunity is lowered. Furthermore, from further tests it has also been found that the above-mentioned activity of the SF-1130-$x_1$ and -$x_2$ substances is also effective to reverse the immunosuppressive effect of an anti-tumor agent such as cyclophosphamide [a preparation of N,N-bis (2-chloroethyl)tetrahydro-2H-1,3,2-oxazophosphorin-2-amine-2-oxide] and completely restore the immune reactivity of living animals. Accordingly, it is clear that the SF-1130-$x_1$ and -$x_2$ substances have an immunomodulating activity in living animals. Results of further similar tests have revealed that the additional use of a maltodextrin, particularly maltopentaose, and maltohexaose improves significantly the activity of the SF-1130-$x_1$ and -$x_2$ substances to enhance the immune reactivity.

The tests were carried out by the following procedure: groups of ICR-JCL strain mice (six male mice per group, average body weight 31.9±3 g.) were inoculated with the ascites tumor "Sarcoma 180" ($10^6$ cells).

24 Hours after the inoculation of the tumor cells, each of the drug samples to be tested was subcutaneously administered and a known anti-tumor agent (cyclophosphamide) was intraperitoneally administered to the inoculated mice. Two days after the inoculation, an ethanolic solution of 5% picryl chloride was applied onto the hair-shaved abdomen of the mice to establish the sensitization. Subsequently, each drug sample under test was subcutaneously administered once a day for the successive four days. 4 Days after the inoculation, cyclophosphamide was again administered. Nine days after the inoculation, a solution of 1% picryl chloride in olive oil was challenged onto the two sides of both ears of the mice to establish the secondary sensitization. 24 Hours after the secondary sensitization, the degree (%) of increase in thickness of the ears was calculated for the test mice. The extent of the swelling which serves as a measure of stimulating cell-mediated immunity involved can be evaluated from the percentage increase in the ear thickness. The sample of the SF-1130-x substance used in this test was a mixture of the SF-1130-$x_1$ and SF-1130-$x_2$ substances in a ratio of 1:2 by weight. The test results obtained are summarized in Table 3 below.

Table 3

| Drug sample administered | Dosage (mg/kg) | Degree of increase in ear thickness($\times 10^{-3}$cm) | percentage increase |
|---|---|---|---|
| SF-1130-x | 100 | 9.2 ± 1.88 | 119.5 |
| SF-1130-x + cyclophosphamide | 100 + 75 | 10.4 ± 4.55 | 135.1 |
| SF-1130-x + maltohexaose | 100 + 200 | 10.4 ± 3.12 | 135.2 |
| SF-1130-$x_2$ | 100 | 9.8 ± 2.03 | 127.2 |
| Cyclophosphamide | 75 | 4.0 ± 2.60 | 51.9 |
| Untreated | — | 7.7 ± 2.06 | 100.0 |

Further tests using solid tumor of Sarcoma 180 were carried out to show that the SF-1130-$x_2$ substance of this invention is active to enhance the immune response in living animals. The tests were conducted by the following procedure: groups of ICR-strain mice (five male mice per group, average body weight 20±2 g.) were inoculated subcutaneously in the flank with a cell suspension of Sarcoma 180 ($7\times 10^6$ cells/0.05 ml.). Six days and five days before the inoculation of the tumor cells to these mice, they were administered intraperitoneally a mixture of the SF-1130-$x_2$ and maltopentaose in a ratio of 1:9 by weight obtained in Example 2. 10 days after the inoculation, the tumor formed was removed from the mice body and the size and weight of the primary subcutaneous tumor were determined. The test results obtained are shown in Table 4 below, from which it will be found that predosing with the SF-1130-$x_2$ substance of this invention prior to the inoculation of Sarcoma 180 brings about a significant inhibition of growth of the solid tumor.

In a separate experiment, male ICR-strain mice (five in each group with an average body weight of 20±2 g) were inoculated in the flank with $7\times 10^6$ live tumor cells of Sarcoma 180 in 0.05 ml. After 24 hours, each group of mice was treated by intraperitoneal injection of 0.1 ml. of saline or sample dissolved in saline for 5 consecutive days. Seven days after the inoculation, all mice were sacrificed and the primary subcutaneous tumor excised and weighed. The results are shown in Table 4 below. The SF-1130-$x_2$ substance in combination of maltodextrin or mitomycin C showed significant inhibition of tumor growth.

Table 4

| Drug administered | Dosages (mg/kg) | Tumor weight (g) | Tumor size (cm$^3$) | Degree (%) of inhibition to tumor growth |
|---|---|---|---|---|
| SF-1130-$x_2$ + maltopentaose | 200 (predose) | 0.07 | 0.141 | 53.3 |
| SF-1130-$x_2$ + maltopentaose | 100 (predose) | 0.06 | 0.167 | 60.0 |
| SF-1130-x | 20 (predose) | 0.08 | 0.151 | 46.8 |
| Untreated control | 0 | 0.15 | 0.326 | — |
| SF-1130-$x_2$ + maltopentaose | 200 | 0.26 | | 66 |
| SF-1130-$x_2$ + maltopentaose | 100 | 0.28 | | 64 |
| SF-1130-$x_2$ + maltopentaose + mitomycin C | 100+2 | 0.24 | | 69 |
| Mitomycin C | 2 | 0.43 | | 45 |
| Untreated control | — | 0.78 | | |

In the above table, degree (%) of inhibition to the growth of tumor was calculated according to the following equation:

$$\% \text{ Inhibition} = \left(1 - \frac{\text{Sample tumor weight}}{\text{Control tumor weight}}\right) \times 100$$

In other tests, the ICR-strain mice was intraperitoneally inoculated with Sarcoma 180 to develop the ascites tumor. After the development of the tumor, the SF-1130-x substance was intraperitoneally administered to the tumor-attacked mice, when it was found that the SF-1130-x substance exhibited no favorable effect in the curative treatment of the Sarcoma 180 tumor. This suggested no significant cidal activity of SF-1130-x substance against tumor cells. Accordingly, it has been elucidated that the SF-1130-x substance is able to activate or enhance the immune resistance of the host to the Sarcoma 180 tumor, so that an apparent therapeutic effect of the SF-1130-x substance against the tumor is only due to the immunopotentiating effect.

Recently, it has been found that protozoan-infected patients and tumor-bearing patients have a considerably reduced immune response as compared to normal persons which neither suffer from the protozoan infection nor from the attack of tumors, and immunotherapy begins to be applied in clinical practice in such a manner that restoration of the impaired immunological response may favor the therapeutic effect of a drug administered. For this application, there is known the use of such immune activators as the bacterial cells of BCG vaccine, as well as various polysaccharides which are all of high molecular weights. As no report has been made, it is surprising that the SF-1130-x substance of this invention, which is an oligo-saccharide of a relatively lower molecular weight of ten or less thousands, is effective to activate the immunological system. It is clear that the use of oligo-saccharides of relatively lower molecular weights is more beneficial in practice than the use of the poly-saccharides, because the oligo-saccharides are normally more easily absorbed by and excreted from living animals, are less causative of undesired allergic reactions and free from the risk of tuberculosis.

Still further tests reveal that the SF-1130-x substance of this invention has an activity to protect animals from bacterial infections. The tests were carried out as follows: the SF-1130-x substance obtained in Example 1 (that is, a mixture of the SF-1130-$x_1$ and -$x_2$ substances in a ratio of 1:2 by weight) was dissolved in a phosphate-buffered saline (pH 7.2) to a concentration of 0.1 or 0.5% of the SF-1130-x substance, and the resulting solution of the SF-1130-x substance was intraperitoneally administered to the test mice at a dosage of 50 mg/kg/day/0.2 ml. or 10 mg/kg/day/0.2 ml. three times at a time interval of 48 hours. The test mice used were JCL:ICR-strain mice (eight male mice per group, average body weight 20 g.). 72 Hours after the final administration, the mice were intraperitoneally inoculated with 0.5 ml./mouse of a cell suspension of *Staphylococcus aureus* Smith S-424 strain which had been prepared by dilution the incubated culture of said strain with physiological saline solution followed by addition of 5% mycin. The number of the mice survived was counted for five days after the inoculation, and $LD_{50}$ value of the bacterial cells that kills 50% of the host was calculated in each case. Control tests were also made where the treatment with the SF-1130-x substance was omitted.

The test results so obtained are set out in Table 5 below, from which it is found that the administration of the SF-1130-x substance leads to an increase in the $LD_{50}$ value of the bacterial cells by approx. 11.4 times at a dosage of 50 mg/kg and by approx. 8.1 times at a dosage of 10 mg/kg of the SF-1130-x substance, as compared to the control tests, showing that the SF-1130-x substance has the preventative effect against the bacterial infection in spite of the fact that the SF-1130-x substance itself has no antibacterial activity against *Staphylococcus aureus* as shown in Table 2 hereinbefore.

Table 5

| Dosage of SF-1130-x substance | Survival of mice at various doses of bacteria inoculated(cells/mouse) | | | | $LD_{50}$ of bacterial cells |
|---|---|---|---|---|---|
| | $9.3 \times 10^7$ | $1.9 \times 10^7$ | $3.7 \times 10^6$ | $7.4 \times 10^5$ | |
| 50 mg/kg | 5/8 | 5/8 | 7/8 | 8/8 | $2.4 \times 10^7$ |
| 10 mg/kg | 1/8 | 3/8 | 7/8 | 7/8 | $1.7 \times 10^7$ |
| Control | — | 0/8 | 2/8 | 8/8 | $2.1 \times 10^6$ |

It is known that some immune activators are sometimes effective in treatment of a disease due to auto-immunization, such as rheumatism. From the following tests, it has been found that the SF-1130-x substance is significantly effective to prevent the development of experimental arthritis which has been considered to have some relationship with the rheumatism. The tests were conducted in the following manner: A cell suspension containing 5.8 mg/ml of *Mycobacterium butyricum* in physiological saline was injected into the right sole foot pad of SD-strain rats (10 female rats per group, average body weight 180 g.) to develop the inflammation. One day after the injection of the bacteria, a solution of 27 mg/ml of the SF-1130-x substance (a mixture of the SF-1130-$x_1$ and SF-1130-$x_2$ substances in a ratio of 1:2 by weight) in a phosphate-buffered saline (pH 7.2) was injected subcutaneously at a dosage of 150 mg/kg/day for the successive 11 days. 14 Days after the bacteria inoculation, the symptons of inflammation which developed in legs, ears, nose, eyes and tail of the treated rats were evaluated in term of scores: 0, 1, 2 and 3, and the average scores are recorded. Furthermore, the volume of the left sole foot pad was determined to estimate the anti-inflammation activity of the SF-1130-x substance. For comparison, phenylbutazone in place of the SF-1130-x substance was orally administered at a dosage of 20 mg/kg/day for the successive 11 days. Further, control tests were conducted in the same manner as above, except that the administration of the SF-1130-x substance and phenylbutazone was omitted. The test results obtained are shown in Table 6 below, from which it is found that the SF-1130-x substance is significantly effective to prevent the experimental arthritis.

The SF-1130-$x_1$ and SF-1130-$x_2$ substances of this invention, either each alone or in mixture, may be formulated into injectable solutions by dissolving at a suitable level into a physiological saline solution or other conventional pharmaceutically acceptable liquid vehicle such as aqueous vehicles, for example, Ringer's injection, dextrose injection, refined oils of vegetable origin or of synthetic mono- or di-glycerides in forms of fat-emulsion, or pharmaceutically acceptable solid vehicles such as suppository cacao or porous polyethylene tube. Thus, for administration of the SF-1130-$x_1$ and SF-1130-$x_2$ substances, the injectable solution so prepared may be given by intravenous drip, local injection, intramuscular injection, intrapleural injection or intraperitoneal injection or as a suppository. As an immunopotentitor, the SF-1130-$x_1$ and SF-1130-$x_2$ substances may be administered at a dosage of approximately 10 to 400 mg/kg/day and preferably of about 50–100 mg/kg/day every day or two or three times a week, alone or in admixture or in combination of antibacterial or antitumor or other immunostimulating agents. As an antibacterial agents, a higher dose, over 400 mg/kg/day will be necessary.

According to a further aspect of this invention, therefore, there is provided a host defense stimulator, that is, an agent for mainly enhancing the immune response in living animals, including men, which comprises as the active ingredient at least one of the SF-1130-$x_1$ substance and SF-1130-$x_2$ substance, in combination with a known pharmaceutically acceptable aqueous or non-aqueous carrier for the active ingredient. Aqueous carrier includes Ringer's injection and injectable nutrient solution such as dextrose and sodium chloride injection, and non-aqueous carrier includes water-in-oil emulsion consisting of 65% sesame oil, 5% Span 80 and 30% aqueous solution of SF-1130-x; oil-in-water emulsion consisting of 30% sesame oil, 65% aqueous solution of SF-1130-x and 5% Tween 80; and water-in-oil emulsion consisting of 9% aqueous solution of SF-1130-x, 19.5% sesame oil, 1.5% Span 80, 65% distilled water and 5% Pluronic F-68. The agent of this invention may effectively be used to prevent a reduction in the immune resistance which would normally be involved by the development and formation of tumors or by the administration of an immunosuppressive anti-tumor agents. Furthermore, the agent of this invention may contain additionally at least one of maltose, maltotriose, maltotetraose, maltopentaose, maltohexaose and maltoheptaose in a proportion sufficient to improve the activity of the SF-1130-$x_1$ substance and/or the SF-1130-$x_2$ substance. The proportion of maltose, maltotriose or other maltodextrin incorporated is 0.1 to 20, preferably 0.5 to 10 parts by weight per one part of the SF-1130-$x_1$ and -$x_2$ substances.

The host defense stimulator of this invention may, if desired, contain at least one of the known antibacterial agents, anti-tumor agents and the other immuno-potentiating agents, with or without a maltodextrin, in addition to the SF-1130-$x_1$ substance and/or the SF-1130-$x_2$ substance. From the foregoing, it is clear that the SF-1130-x substance serves for prophylactic use against bacterial infection, tumor and rheumatics.

This invention is now illustrated with reference to the following Examples to which this invention is not limited.

EXAMPLE 1

A seed culture of *Streptomyces myxogenes* SF-1130 (identified as FERM-P. 676 or ATCC. 31305) was inoculated to 200 l. of a liquid culture medium comprising 5.0% starch syrup, 2.5% soybean meal, 1.0% wheat embryo and 0.25% sodium chloride. The inoculated medium was incubated in a jar-fermentor under aeration and agitation at 28° C. for 64 hours.

At the end of the incubation, the resultant culture broth was adjusted to pH 3 by addition of hydrochloric acid and then filtrated under the acidic conditions to give 140 l. of the broth filtrate. This filtrate was passed through a column of 20 l. of a strongly acidic cation-exchange resin, Dowex 50W×2 (H+ form) (a product made by Dow Chemical Co., U.S.A.) for the adsorption of the SF-1130-$x_1$ and -$x_2$ substances by the resin. After thorough washing with water, the resin column was eluted with totally 80 l. of 0.1 N aqueous ammonia. The eluate was collected in fractions, and such fractions which showed antibacterial activity against *Escherichia coli* K-12R were combined together and concentrated to dryness to obtain 250 g of a brown-colored powder.

The effluent (150 l.) which passed directly out of the above resin column upon the passage of the broth filtrate therethrough was again acidified to pH 3.0 by addition of hydrochloric acid and then placed into a column of 20 l. of Dowex 50W×2 ($H^{30}$ form) for the adsorption of the remaining active substances. The resin column was well washed with water and then eluted with totally 80 l. of 0.1 N aqueous ammonia. The eluate was again collected in fractions, and such fractions active against *E. coli* K-12R were combined together and concentrated to dryness to obtain 51 g of a brown colored powder as a second crop.

The brown-colored powder (47 g) obtained as the first crop was dissolved in 250 ml. of water, followed by adjustment to pH 3.0 by addition of hydrochloric acid. The acidic solution so obtained was passed through a column (5.5×26 cm) of 600 ml. of active carbon (a product made by Wako Junyaku Co., Japan) for adsorption of the active substances. The carbon column was washed with water and eluted with an aqueous solution of 30% ethanol and then with an aqueous solution of 35% ethanol. The eluate was collected in fractions, and those active fractions which showed antibacterial activity against *E. coli* K-12R were combined together-(4 l.) and concentrated to dryness to give 5.6 g of a yellowish brown powder.

This powder was again taken up into 100 ml. of water, followed by adjustment to pH 3 by addition of hydrochloric acid. The acidic solution so obtained was passed through a column of 600 ml. of Dowex 50W×2 ($NH_4^+$ form) for the adsorption of the active substances. This resin column was well washed with water and then eluted with 0.1 N aqueous ammonia. The eluate was collected in fractions, and the fractions active against *E. coli* K-12R were combined together and concentrated to dryness to obtain 1.5 g of a yellowish-brown powder.

A part (1 g) of this powder was dissolved in 70 ml. of a buffer solution (0.1 M pyridine-formic acid solution, pH 3.1), and the resulting solution was placed in a column (3.5×60 cm) of 500 ml. of Dowex 50W×2 (pyridinium form, 200–400 mesh) for the adsorption of the active substances. The resin column was then eluted with the same buffer solution as above and the eluate was collected in 10 ml.-fractions. The antibacterially active fraction Nos. 63–79 which each gave a single spot colored by the silver nitrate reagent at an $R_{alanine}$ value of 0.53 (calculated with assumption that the $R_f$ value of alanine is 1.00) in a high-voltage filter paper electrophoresis were combined together and concentrated to dryness to yield 380 mg of a colorless powder comprising the SF-1130-x substance as a mixture of the SF-1130-$x_1$ and SF-1130-$x_2$ substances.

This colorless powder was dissolved in a small volume of water and the resultant aqueous solution was admixed with a mixed solvent of n-propanol-ethyl acetate-water (6:1:3 by volume). The admixture was passed through a column (3×30 cm) of 200 ml. of cellulose for the adsorption of the active substances, and the cellulose column was eluted with the same mixed solvent as above. The eluate was collected in 7 ml.-fractions, and each fraction was tested by paper-chromatography using a mixed solvent of ethyl acetate-pyridine-water (10:4:3 by volume) as the developing solvent. Those antibacterially active fraction Nos. 351–445 which each gave a single spot colored by the silver nitrate reagent at an $R_{raffinose}$ value of 0.57 (calculated as assumed that the $R_f$ value of raffinose is 1.00) in the above paper-chromatography were combined together and concentrated to dryness to afford 150 mg of a colorless powder comprising the SF-1130-$x_2$ substance.

At the same time, those antibacterially active fraction Nos. 503–550 which each gave a single spot colored by the silver nitrate reagent at an $R_{raffinose}$ value of 0.39 as defined above in the same paper-chromatography were combined together and concentrated to dryness to afford 70 mg of a colorless powder comprising the SF-1130-$x_1$ substance.

The colorless powder (150 mg) comprising the SF-1130-$x_2$ substance was dissolved in 6 ml. of water and the resulting aqueous solution was passed into a column (2×5.5 cm) of 15 ml. of active carbon for the adsorption of the active substance. The carbon column was washed with water and then eluted with an aqueous solution of 30% ethanol and then with an aqueous solution of 35% ethanol. The eluate was collected in 3 ml.-fractions. The antibacterially active fraction Nos. 30 to 42 were combined and concentrated to dryness to afford a pure product of the SF-1130-$x_2$ substance as colorless powder having a melting point of 195° C. (with decomposition). Yield 120 mg. The colorless powder (70 mg) comprising the SF-1130-$x_1$ substance was processed in the same way as above to afford a pure product of the SF-1130-$x_1$ substance as a colorless powder having a melting point of 203° C. (with decomposition). Yield 55 mg.

The brown powder (51 g) obtained as the above-mentioned second crop from the eluate which was passed directly out of the second column of Dowex x 50W×2 (H+ form) eluted with 0.1 N aqueous ammonia was also subjected to the same purification and isolation procedures as above, to recover 210 mg of a pure product of the SF-1130-x₁ substance and 520 mg of a pure product of the SF-1130-x₂ substance.

EXAMPLE 2

A seed culture of *Streptomyces myxogenes* SF-1130 (identified as FERM-P. 676 or ATCC. 31305) was inoculated to 20 l. of the liquid culture medium of the same composition as that used in Example 1. The incubation was made in a jar-fermentor at 28° C. for 66 hours under aeration and agitation.

At the end of the incubation, the fermentation broth was adjusted to pH 3.0 by addition of hydrochloric acid and filtered under the acidic conditions to give 15 l. of the broth filtrate. This filtrate was passed through a column (6×36 cm) of 1 l. of active carbon (a product made by Wako Junyaku Co., Japan) for the adsorption of the active substances. The carbon column was thoroughly washed with water and then eluted with 5 l. of an aqueous solution of 50% acetone at pH 8, and such fractions active against *E. coli* K-12R (150 ml.) were taken up, combined together and concentrated to dryness to give 67.5 g of a yellowish-brown powder.

A portion (45 g) of this powder was taken up into 200 ml. of water and the resulting aqueous solution was placed in a column (5.6×42 cm) of 1 l. of active carbon for the adsorption of the active substances. The carbon column was washed with water and then eluted successively with aqueous solutions containing 5%, 10%, 15%, 20% and 25% ethanol. The eluate was collected in 15 ml.-fractions. The antibacterially active fractions Nos. 366–510 were combined and concentrated to dryness to give 5.7 g of a colorless powder.

This colorless powder (5 g) was dissolved in 15 ml. of water and the solution so obtained was filtered. To the filtrate was slowly added 180 ml. of ethanol to cause reprecipitation.

The precipitate was removed by filtration and vacuum-dried to yield 4.6 g of a colorless powder comprising a mixture of 10% by weight of the SF-1130-x₂ substance and 90% by weight of maltopentaose.

What we claim is:

1. A process for the production of SF-1130-x₁ substance and SF-1130-x₂ substance, which comprises cultivating a strain of the genus *Streptomyces myxogenes* SF-1130 identifiable as FERM-P. 676 or ATCC 31,305 capable of producing SF-1130-x₁ substance and/or SF-1130-x₂ substance in an aqueous liquid culture medium containing assimilable carbon and nitrogen sources under aerobic conditions for a period of time sufficient to produce and accumulate the SF-1130-x₁ substance, the SF-1130-x₂ substance or both of them in the culture, and then recovering a pure product consisting essentially of at least one of the SF-1130-x₁ substance and SF-1130-x-₂ substance from the culture.

2. A process according to claim 1 in which a mixture of the SF-1130-x₁ and SF-1130-x₂ substances is recovered from the culture broth of said *Streptomyces myxogenes SF-*1130.

Figure 1A:
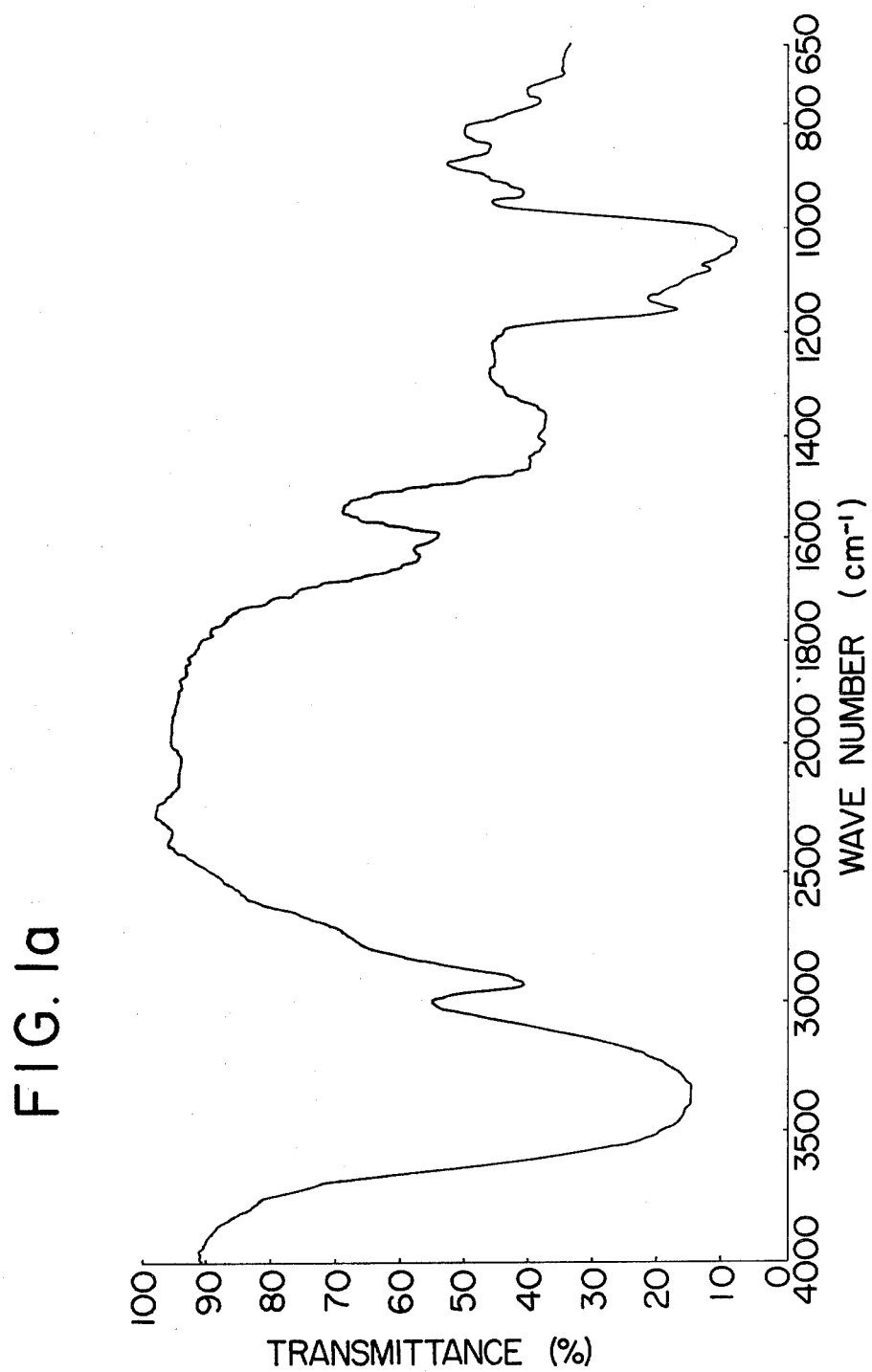
FIG. 1a shows a curve of the infrared absorption spectrum of sample of the SF-1130-$x_1$ substance according to this invention pelleted in potassium bromide.
Figure 1B:
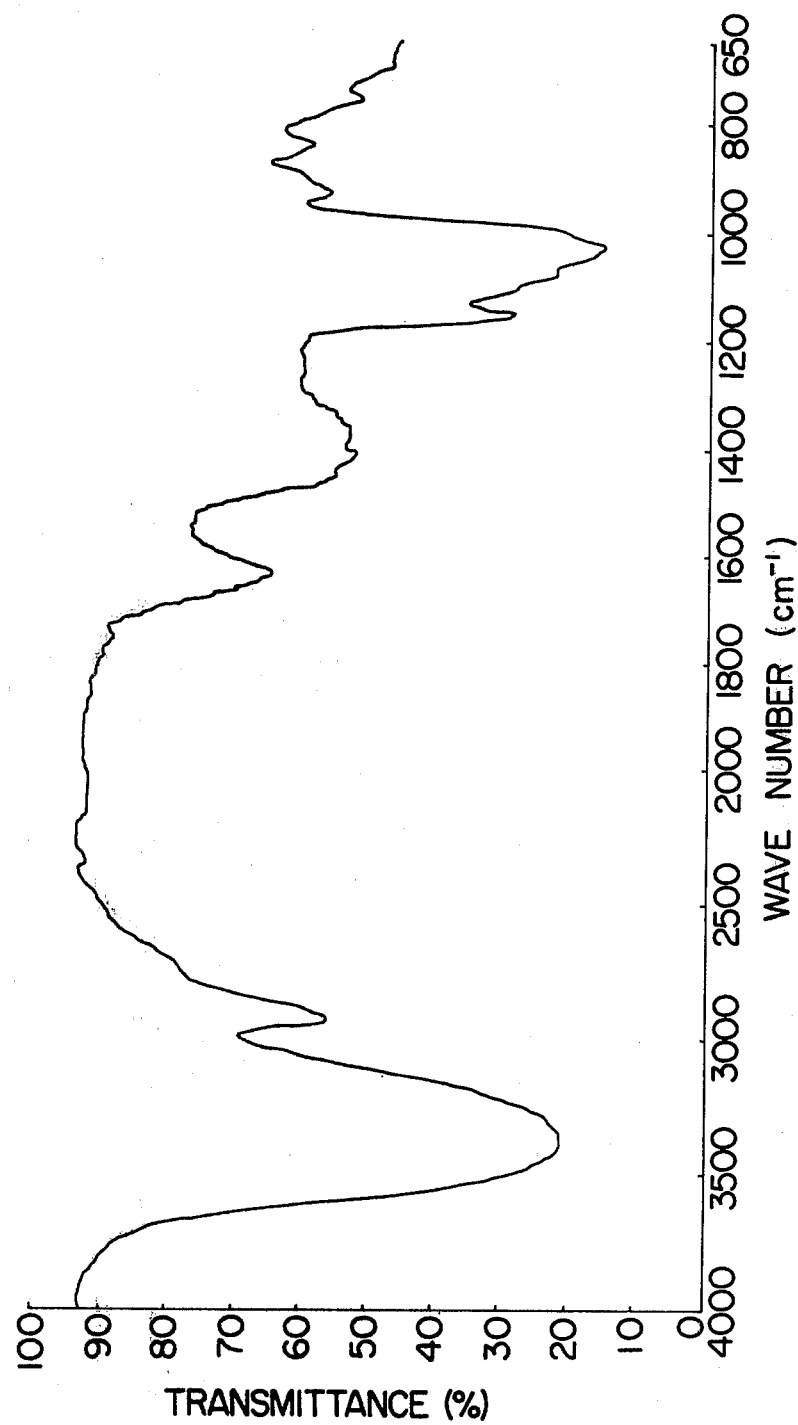
FIG. 1b shows a curve of the infrared absorption spectrum of sample of the SF-1130-$x_2$ substance according to this invention pelleted in potassium bromide.

3. A substance selected from the group consisting of SF-1130-x₁ substance and SF-1130-x₂ substance which are each an oligo-saccharide of weakly basic nature in the form of a colorless powder, which are each soluble in water and dimethylsulfoxide, less soluble in methanol and ethanol but insoluble in acetone, ethyl acetate, chloroform and benzene, which each show positive reaction with silver nitrate, red tetrazolium, anthrone, ninhydrin and Grieg-Leaback reagents and which are each hydrolyzable with acid to give glucose; the SF-1130-x₁ substance being further characterized by:

(a) exhibiting an elemental analysis: C 43.65% H 6.55%, N 1.05% and O 49.75% (balance);
(b) having a specific optical rotation $[\alpha]_D^{23} + 166°$ (c 1 in water);
(c) having no characteristic absorption peak in ultraviolet spectrum;
(d) having an infrared absorption spectrum pelleted in potassium bromide corresponding to that shown in FIG. 1a of the attached drawings;
(e) having a hydrogen nuclear magnetic resonance absorption spectrum in deutero-water corresponding to that shown in FIG. 2a of the attached drawings; and
(f) giving a single spot at $R_{raffinose}=0.39$ in paper-chromatography with ethyl acetate-pyridine-water (10:4:3) as the developing solvent and at $R_{raffinose}=0.19$ in paper-chromatography with n-butanol-pyridine-acetic acid-water (6:4:1:3) as the developing solvent when the $R_{raffinose}$ values are calculated as assumed that raffinose gives a single spot at Rf=1.00 in the same paper chloromatography; and the SF-1130-x₂ substance being further characterized by:

(a) exhibiting an elemental analysis: C 43.84%, H 6.41%, N 1.08% and O 49.67% (balance);
(b) having a specific optical rotation $[\alpha]_D^{23} + 155°$ (c 1 in water);
(c) having no characteristic absorption peak in ultraviolet absorption spectrum;
(d) having an infrared absorption spectrum pelleted in potassium bromide corresponding to that shown in FIG. 1b of the attached drawings;
(e) having a hydrogen nuclear magnetic resonance spectrum in deutero-water corresponding to that shown in FIG. 2b of the attached drawings; and
(f) giving a single spot at $R_{raffinose}=0.57$ in paper-chromatography with ethyl acetate-pyridine-water (10:4:3) as the developing solvent and at $R_{raffinose}=0.33$ in paper-chromatography with n-butanol-pyridine-acetic acid-water (6:4:1:3) as the developing solvent when the $R_{raffinose}$ values are calculated as assumed that raffinose gives a single spot at $R_f=1.00$ in the same paper chromatography.

4. A substance according to claim 3 which is the SF-1130-x₁ substance as defined in claim 3.

5. A substance according to claim 3 which is the SF-1130-x₂ substance as defined in claim 3.

6. A substance according to claim 3 which is the form of a mixture of the SF-1130-x₁ and SF-1130-x₂ substances.

7. A host defence stimulator for enhancing mainly the immune response in living animals which comprises as the active ingredient at least one of the SF-1130-x₁ substance and SF-1130-x₂ substance as defined in claim 3, in combination with a known pharmaceutical acceptable carrier for the active ingredient.

8. A host defense stimulator according to claim 7, which contains additionally at least one of maltose, maltotriose, maltotetraose, maltopentaose, maltohexaose and meltoheptaose in an amount sufficient to significantly improve enhancement of immune reactivity by the SF-1130-x₁ and SF-1130-x₂ substances.

9. A host defense stimulator according to claim 8, which contains at least one of known antibacterial agents, anti-tumor agents and immunopotentiating agents in addition to the SF-1130-$x_1$ and/or the SF-1130-$x_2$ substance.

10. A host defense stimulator according to claim 9 further containing 0.1 to 20 parts by weight of a maltodextrin per part by weight of the SF-1130-$x_1$ and SF-1130-$x_2$ substance.

11. A process for stimulating the immune response in a living animal, which comprises administering a safe and immunopotentiatingly effective amount of at least one of the SF-1130-$x_1$ substance and SF-1130-$x_2$ substance as defined in claim 3 to said animal.

* * * * *